United States Patent [19]
Roberts

[11] 4,093,975
[45] June 6, 1978

[54] HIGH-VOLTAGE APPARATUS FOR SKIN THERAPY

[76] Inventor: Wallace A. Roberts, 88 N. Main St., Bellingham, Mass. 02019

[21] Appl. No.: 757,041

[22] Filed: Jan. 5, 1977

[51] Int. Cl.² ............................................. H02M 5/44
[52] U.S. Cl. ........................................ 363/27; 363/37; 128/419 R
[58] Field of Search ................. 307/240; 128/419 PG, 128/420, 421; 321/2, 43, 44, 47; 323/22 SC; 363/27, 85, 86, 37

[56] References Cited
U.S. PATENT DOCUMENTS

| | | | |
|---|---|---|---|
| 3,248,634 | 4/1966 | Fudaley et al. | 321/2 |
| 3,259,893 | 7/1966 | Parker | 307/252 J X |
| 3,304,486 | 2/1967 | Michaels | 323/22 SC X |
| 3,500,168 | 3/1970 | Merritt | 321/21 X |
| 3,639,826 | 2/1972 | Grundberg | 321/2 |
| 3,838,328 | 9/1974 | Lundy | 321/2 |
| 3,839,668 | 10/1974 | Black | 321/21 |
| 3,842,334 | 10/1974 | Franz, Jr. | 321/2 |

*Primary Examiner*—William M. Shoop
*Attorney, Agent, or Firm*—William Nitkin

[57] ABSTRACT

An apparatus for skin therapy employs a circuitry for generating a high voltage that is connected to an electrode. The circuitry to step up voltage from a power supply includes a transistor, transformer and rectifier; and the means to control application of the stepped up voltage to an electrode coil or transformer includes a silicon controlled rectifier in series with a capacitor and an output transformer's primary. Pulsing means, having voltage supplied from a power source on a separate circuit, to control the rate of silicon controlled rectifier firing and therefore discharge of the capacitor includes a unijunction oscillator and transistor. The output transformer's secondary powers the electrode.

1 Claim, 1 Drawing Figure

HIGH FREQUENCY GENERATOR

HIGH-VOLTAGE APPARATUS FOR SKIN THERAPY

BACKGROUND OF THE INVENTION

The present invention relates to a therapeutic high voltage generator capable of producing in an electrode a high frequency static charge. More particularly the present invention relates to solid state circuitry which, by rapid oscillation of voltage pulses causes a silicon controlled rectifier to fire a stepped up DC voltage to an output transformer.

Production of a static charge by means of high frequency voltage generation has been applied for certain therapeutic purposes such as treating various types of skin disorders, including acne. The static charge is produced by an electrode, discharging to a subject's skin, which electrode contains a gas or gases capable of ionization by a high voltage current. To make the application safe with as little discomfort as possible it is necessary to create the static charges in rapid, short bursts.

To create the high voltage generation and rapid burst delivery, electromechanical generation means have been utilized in the prior art. An electric circuit would be utilized to step up the voltage and the pulsing bursts would be created by a mechanical type of vibrator. The vibrator being mechanical in nature places limitations upon the frequency of the bursts and thus the frequency of the static charge and its intensity. The frequency of such units is in the range of 1,000 cycles per sec. Large, strong sparks can be created and cause discomfort. It has been found that a short, high voltage, high frequency static charge creates a mild sensation with lessened subject discomfort.

Further, electromechanical generators have a relatively short life span, with circuit malfunction due to the mechanical aspects of the unit. Also these units tend to be noisy and cumbersome. Features and distinctions in contrast to the prior art will become apparent in reference to the following objects and advantages of the present invention.

SUMMARY

It is an object of the present invention to rapidly pulse a short burst of high voltage static energy discharged to a body from an ionized electrode.

It is a further object to produce high voltage generation by means of solid state circuitry which creates high frequency static discharges which cause a mild sensation and relatively little discomfort to a subject.

The present invention contemplates circuitry which steps up voltage from a power source which is rapidly intermittently delivered by a unidirectional thyristor means to an output transformer connected with the output electrode. The unidirectional thyristor, which is preferably a silicon controlled rectifier, is controlled by an oscillating circuit which rapidly pulses, and causes the silicon control rectifier to fire.

Due to its solid state design the present invention has long life and is compact and quiet. Patient discomfort is minimized and safety of the treatment process is enhanced due to the short bursts of static energy rather than large, strong bursts. Further features and advantages will become apparent with reference to the following drawing and description thereof.

DESCRIPTION OF THE PREFERRED EMBODIMENT

Figure 1:
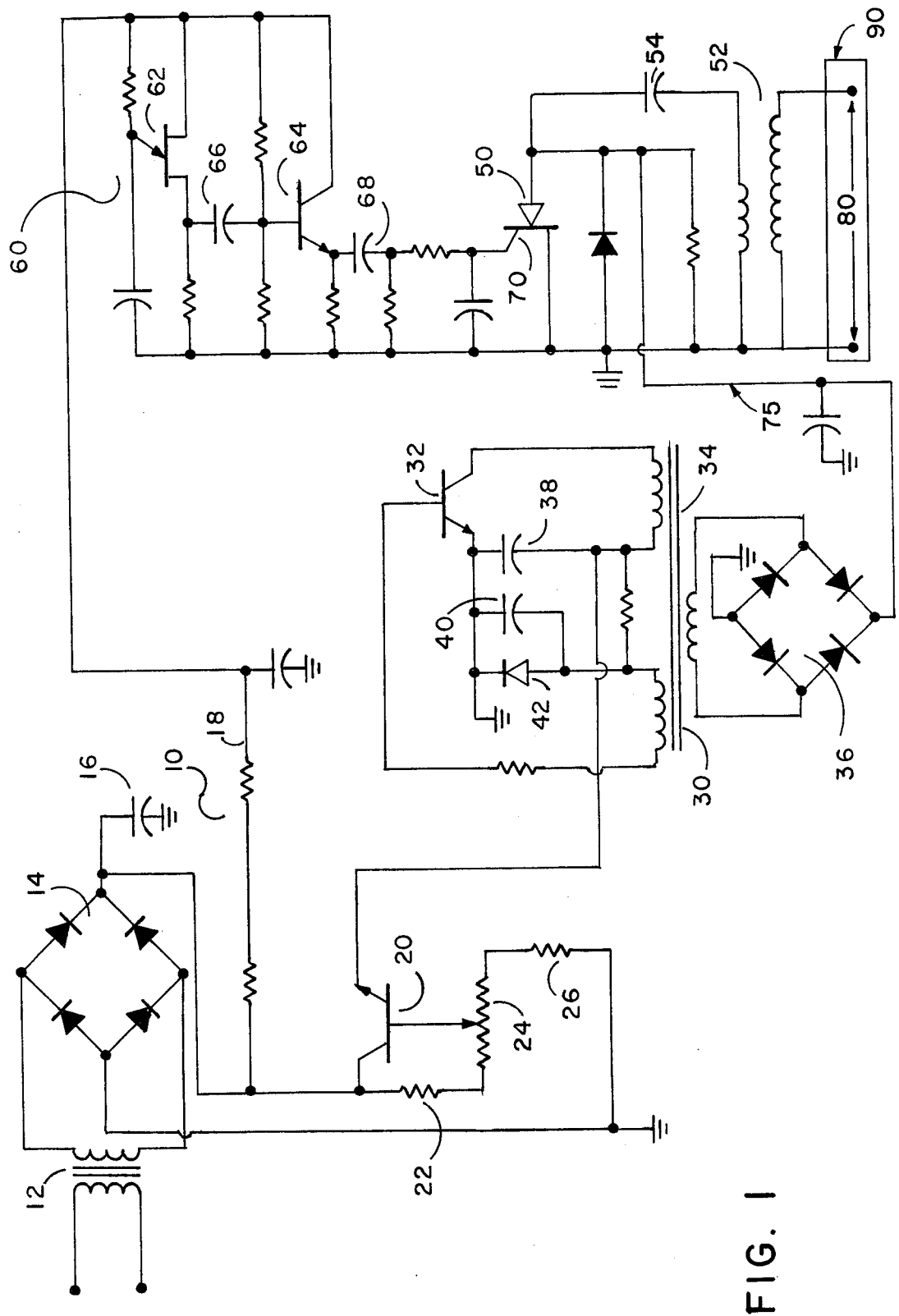
FIG. 1 is a schematic diagram illustrating the high frequency generation circuitry of the present invention.

Referring now in detail to the drawing, preferred power supply circuitry is designated generally by the numeral 10. With respect to the present invention it is only essential that the high frequency voltage generation circuitry output have two circuit sources with the initial voltage of one circuit source being variable from a power supply source. The variable voltage is desired to allow an operator to control the output intensity of the static charge. A constant current of 16 volts is supplied to a pulsing circuit. A variable current level ranging from 0 to 14 volts is supplied to circuit 30 and is to be initially stepped up to 400 to 600 volts and ultimately stepped-up and increased to a static charge output in the range of 40,000 to 60,000 volts.

To produce this output, the present invention contemplates the utilization of transformer 12 having approximately 12.6 volt output which is delivered to bridge rectifier circuit 14. Capacitor 16 filters the voltage. Line 18 supplies the current of 16 volts to the pulsing circuit. Transistor 20 also receives voltage from rectifier 14 and in combination with resistors 22, 24, and 26 provides the means to vary the voltage level traveling to what may be deemed a DC-to-DC converter generally designated 30, that voltage level variation being directly proportional to the output static charge voltage variation.

Converter 30 is comprised of three major elements which step up the voltage to 400 – 600 volts; transistor 32, transformer 34 and bridge rectifier 36. Transistor 32 operating in conjunction with capacitors 38 and 40 and with rectifier 42 oscillates the variable level voltage as fed by transistor 20. Across the secondary of transformer 34 is produced 400 – 600 volts AC which rectifier 36 changes to DC. Thereafter this DC 75 output charges a capacitor 54 which through a silicon controlled rectifier 50 or equivalent is caused to discharge into the primary circuit of a high voltage transformer 52. The output 80 of the transformer 52 is used to power the electrode.

Silicon controlled rectifier 50 controls when voltage will be applied to transformer 52 and is caused to fire, and thus controlled, by an oscillating circuit, generally designated 60. Oscillating or pulsing circuitry 60, which receives constant voltage from the power source via line 18, drives silicon controlled rectifier 50 into conduction with each pulse. Oscillating circuit 60 is comprised essentially of unijunction oscillator 62 and transistor 64 which is a buffer amplifier. These elements operate in conjunction with capacitors 66 and 68 to pulse gate 70 of silicon controlled rectifier 50 to activate the SCR. Prior to the point in each cycle when the SCR is driven into conduction, a charge builds up on capacitor 54, which is in series with the output 75 of converter 30 and the primary of transformer 52, through which one side of the capacitor is grounded to complete the circuit. After a charge has accumulated on the capacitor, the SCR is driven into conduction by a pulse from oscillating circuit 60, and the capacitor discharges through the SCR into the primary of the transformer 52. The magnetic field set up by the current flow discharge of the capacitor through the primary causes a high voltage to be induced in the secondary of the transformer 52 and to be available across the output 80 for connection to the electrode. The oscillating circuitry should be designed to pulse in the range of 300,000 times per second with the output transformer being capable of producing an output pulse up to 60,000 volts.

Although the present invention has been described with reference to particular embodiments, it will be apparent to those skilled in the art that variations and modifications can be substituted therefor without departing from the principles and spirit of the invention.

I claim:

1. An improved high voltage apparatus for skin therapy comprising:
    a low voltage DC power source having fixed and variable voltage outputs;
    a DC-to-DC converter, having (i) a converter oscillator powered by the variable voltage output of the DC power source, (ii) a converter step-up transformer, the primary winding(s) of which are fed by the oscillator, (iii) a rectifier circuit connected to the secondary winding of the converter step-up transformer, and (iv) a filter capacitor in shunt across the rectifier output;
    an output transformer;
    a second capacitor, connected in series with the output from the DC-to-DC converter and the primary winding of the output transformer;
    a silicon-controlled rectifier, the anode and cathode of which are connected so as to cause discharge of the second capacitor across the primary winding of the output transformer whenever the silicon-controlled rectifier is triggered into conduction by a suitable pulse between its gate and source;
    a second oscillator, powered by the fixed output of the DC power source;
    an emitter-follower amplifier, also powered by the fixed output of the DC power source, the input of which amplifier is connected to the second oscillator and the output of which is connected to the gate of the silicon-controlled rectifier, so as to trigger the rectifier once per cycle of output of the second oscillator; and
    a skin therapy electrode connected to the secondary winding of the output transformer.

* * * * *